(12) United States Patent
Yao

(10) Patent No.: US 7,175,666 B2
(45) Date of Patent: Feb. 13, 2007

(54) MODULAR IMPLANT WITH A MICRO-MOTION DAMPER

(75) Inventor: Jian Q. Yao, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 177 days.

(21) Appl. No.: 10/837,148

(22) Filed: Apr. 30, 2004

(65) Prior Publication Data
US 2005/0246030 A1 Nov. 3, 2005

(51) Int. Cl.
*A61F 2/38* (2006.01)
(52) U.S. Cl. .................................. 623/20.33
(58) Field of Classification Search ............ 623/22.21, 623/22.14, 20.33, 17.15, 17.13
See application file for complete search history.

(56) References Cited

U.S. PATENT DOCUMENTS

| | | | | |
|---|---|---|---|---|
| 4,309,777 A | * | 1/1982 | Patil | 623/17.13 |
| 4,673,407 A | * | 6/1987 | Martin | 623/20.33 |
| 4,795,468 A | * | 1/1989 | Hodorek et al. | 623/20.28 |
| 5,108,442 A | * | 4/1992 | Smith | 623/20.33 |
| 5,108,447 A | * | 4/1992 | Zeiler et al. | 623/22.14 |
| 5,549,700 A | * | 8/1996 | Graham et al. | 623/22.14 |
| 5,824,101 A | * | 10/1998 | Pappas | 623/20.33 |
| 6,004,352 A | * | 12/1999 | Buni | 623/20.33 |
| 6,126,692 A | * | 10/2000 | Robie et al. | 623/20.32 |
| 6,217,618 B1 | * | 4/2001 | Hileman | 623/20.33 |
| 6,231,609 B1 | * | 5/2001 | Mehdizadeh | 623/17.11 |
| 6,306,172 B1 | * | 10/2001 | O'Neil et al. | 623/20.15 |
| 6,319,283 B1 | | 11/2001 | Insall et al. | |
| 6,475,243 B1 | * | 11/2002 | Sheldon et al. | 623/22.28 |
| 6,569,202 B2 | * | 5/2003 | Whiteside | 623/20.32 |
| 2004/0024460 A1 | * | 2/2004 | Ferree | 623/17.12 |
| 2005/0192674 A1 | * | 9/2005 | Ferree | 623/23.41 |

FOREIGN PATENT DOCUMENTS

EP 0 512 529 A 11/1992

OTHER PUBLICATIONS

Jian Q. Yao et al., "Backside Wear of Conventional and Highly Crosslinked UHMWPE Tibial Inserts as Tested in a Knee Wear Simulator," 29th Annual Meeting of Society for Biomaterials, Apr. 30-May 3, 2003, p. 609, Reno, Nevada, U.S.A.
Zimmer, "NexGen(trademark) Complete Knee Solution Cruciate Retaining Augmentable (CRA)," http://www.zimmer.com/zportal/page?PID=pgBodyLayout.html&XML=zimmer.un-00.en.pr..., Sep. 23, 2002, 4 pages, Internet.
Zimmer, "NexGen(trademark) Complete Knee Solution Legacy(trademark) Knee Posterior Stabilized (LPS)," http://www.zimmer.com/zportal/page?PID=pgBodyLayout.html&XML=zimmer.un-00.en.pr..., Sep. 23, 2002, 2 pages, Internet.

(Continued)

*Primary Examiner*—Alvin J. Stewart
(74) *Attorney, Agent, or Firm*—Baker & Daniels LLP

(57) ABSTRACT

A modular implant is provided. The modular implant includes a first orthopaedic component, a second orthopaedic component coupled to the first orthopaedic component, and a micro-motion damper interposed between the first orthopaedic component and the second orthopaedic component.

9 Claims, 2 Drawing Sheets

OTHER PUBLICATIONS

Zimmer, "NexGen(trademark) Complete Knee Solution Legacy(trademark) Knee Posterior Stabilized (LPS) LPS-Flex Fixed Bearing Knee," http://www.zimmer.com/zportal/page?PID=pgBodyLayout.html&XML=zimmer.un-00.en.pr..., Sep. 23, 2002, 2 pages, Internet.

Zimmer, "NexGen(trademark) Complete Knee Solution Legacy(trademark) Knee Constrained Condylar Knee (LCCK)," http://www.zimmer.com/zportal/page?PID=pgBodyLayout.html&XML=zimmer.un-00.en.pr..., Sep. 23, 2002, 3 pages, Internet.

G. A. Engh et al., "In vivo deterioration of tibial baseplate locking mechanisms in contemporary modular total knee components," http://www.ncbi.nlm.nih.gov/entrez/query.fcgi?cmd=Retrieve&db=PubMed&list_uids=1170..., Sep. 23, 2002, 2 pages, Internet.

S. Miyoshi et al., "Analysis of the shape of the tibial tray in total knee arthroplasty using a three dimension finite element model," http://www.ncbi.nlm.nih.gov/entrez/query.fcgi?cmd=Retrieve&db=PubMed&list_uids=1220..., Sep. 23, 2002. 2 pages, Internet.

S. A. Edwards et al., "Analysis of polyethylene thickness of tibial components in total knee replacement," http://www.ncbi.nlm.nih.gov/entrez/query.fcgi?cmd=Retrieve&db=PubMed&list_uids=1188..., Sep. 23, 2002, 2 pages, Internet.

T. Q. Lee et al., "Effects of screw types in cementess fixation of tibial tray implants: stability and strength assessment," http://www.ncbi.nlm.nih.gov/entrez/query.fcgi?cmd=Retrieve&db=PubMed&list_uids=1061..., Sep. 23, 2002, 2 pages, Internet.

* cited by examiner

US 7,175,666 B2

MODULAR IMPLANT WITH A MICRO-MOTION DAMPER

FIELD OF THE INVENTION

The present invention relates generally to the field of orthopaedics, and, more particularly, to modular implants.

BACKGROUND

Many conventional orthopaedic implant assemblies are modular. Among other things, modularity facilitates the intra-operative versatility of combining various components best suited for any particular patient. However, some modular designs allow small amounts of undesirable motion ("micro-motion") between components that should stay firmly locked together after assembly. Such micro-motion is an undesirable source of wear that can degrade alignment and/or stability of some prostheses over time, or otherwise reduce the useful life of some modular implants.

SUMMARY OF THE INVENTION

The present invention provides a modular implant including a first orthopaedic component, a second orthopaedic component coupled to the first orthopaedic component, and a micro-motion damper interposed between the first orthopaedic component and the second orthopaedic component.

In an alternative embodiment, the present invention provides a knee prosthesis for insertion between a femur and a tibia. The knee prosthesis includes a tibial component. The tibial component includes a first portion configured to be implanted in the tibia and further includes second portion defining a tibial baseplate. The knee prosthesis also includes a bearing coupled to the tibial component and positioned within the tibial baseplate. Further, the knee prosthesis includes a resilient component sandwiched between the tibial component and the bearing.

In another alternative embodiment, the present invention provides an apparatus for forming a prosthetic joint between a first body part and a second body part. The apparatus includes a first means for coupling the prosthetic joint to the first body part, a second means for coupling the prosthetic joint to the second body part, a means for articulating the first means relative to the second means, and a means for damping micro-motion within the prosthetic joint.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

Figure 1:
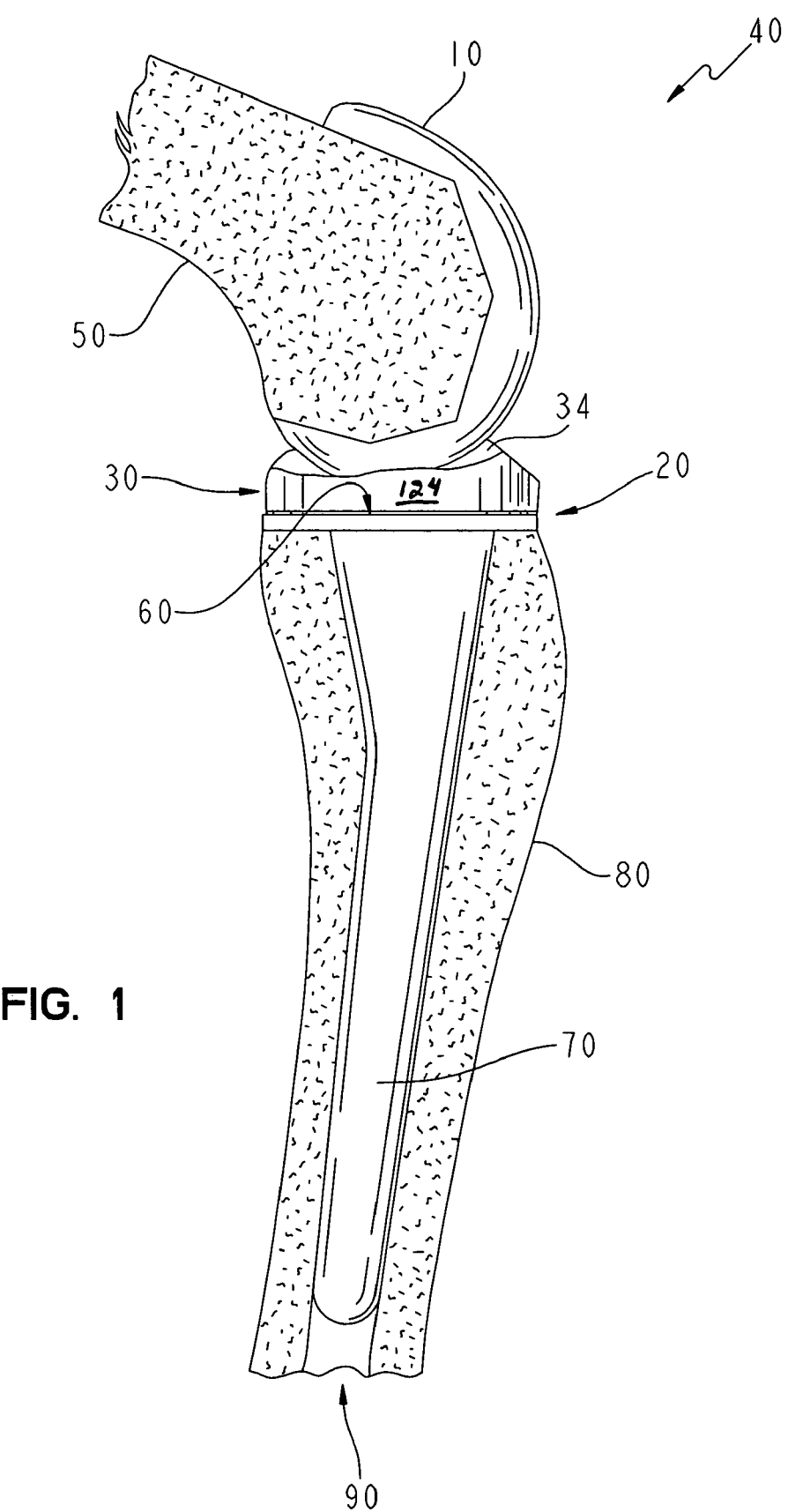
FIG. 1 shows a lateral view of an exemplary modular prosthetic knee assembly according to the present invention.

FIG. 1 shows a lateral view of an exemplary modular prosthetic knee assembly 40 according to the present invention. Knee assembly 40 includes a femoral component 10, a tibial component 20, and a bearing 30. Femoral component 10 is configured in a known manner to fit onto a resected distal femur 50 and is made from a metallic material or alloy such as cast Co—Cr—Mo or any other suitable biocompatible material(s). Tibial component 20 defines a recessed tibial baseplate 60 (see also FIG. 2) with an inner sidewall 64 (not indicated in FIG. 1; but see FIG. 2), and defines an elongated stem 70. Tibial component 20 is configured in a known manner to secure to a proximal tibia 80 via insertion of stem 70 into an intramedullary canal 90 of tibia 80 and is made from a metallic material or alloy such as cast Co—Cr—Mo or any other suitable biocompatible material (s). It should be appreciated that in alternative embodiments, stem 70 may be replaced with any other suitable bone fixation feature(s).

Bearing 30 is configured in a known manner to facilitate articular movement (linear translation and rotation) between femoral component 10 and tibial component 20 (and thus, to facilitate articular movement between femur 50 and tibia 80) and is made from a polymeric material such as ultra-high molecular weight polyethylene ("UHMWPE") or any other suitable biocompatible material(s). Further, bearing 30 includes a substantially planar bottom or distal surface 120 (not indicated in FIG. 1; but see FIG. 2) facing tibial baseplate 60, and includes a sidewall 124. Knee assembly 40 also includes a micro-motion damper 130 (not indicated in FIG. 1), a micro-motion damper 140 (not indicated in FIG. 1), a micro-motion damper 150 (not indicated in FIG. 1), and a micro-motion damper 160 (not indicated in FIG. 1), which are shown in FIG. 2 and discussed further below.

Figure 2:
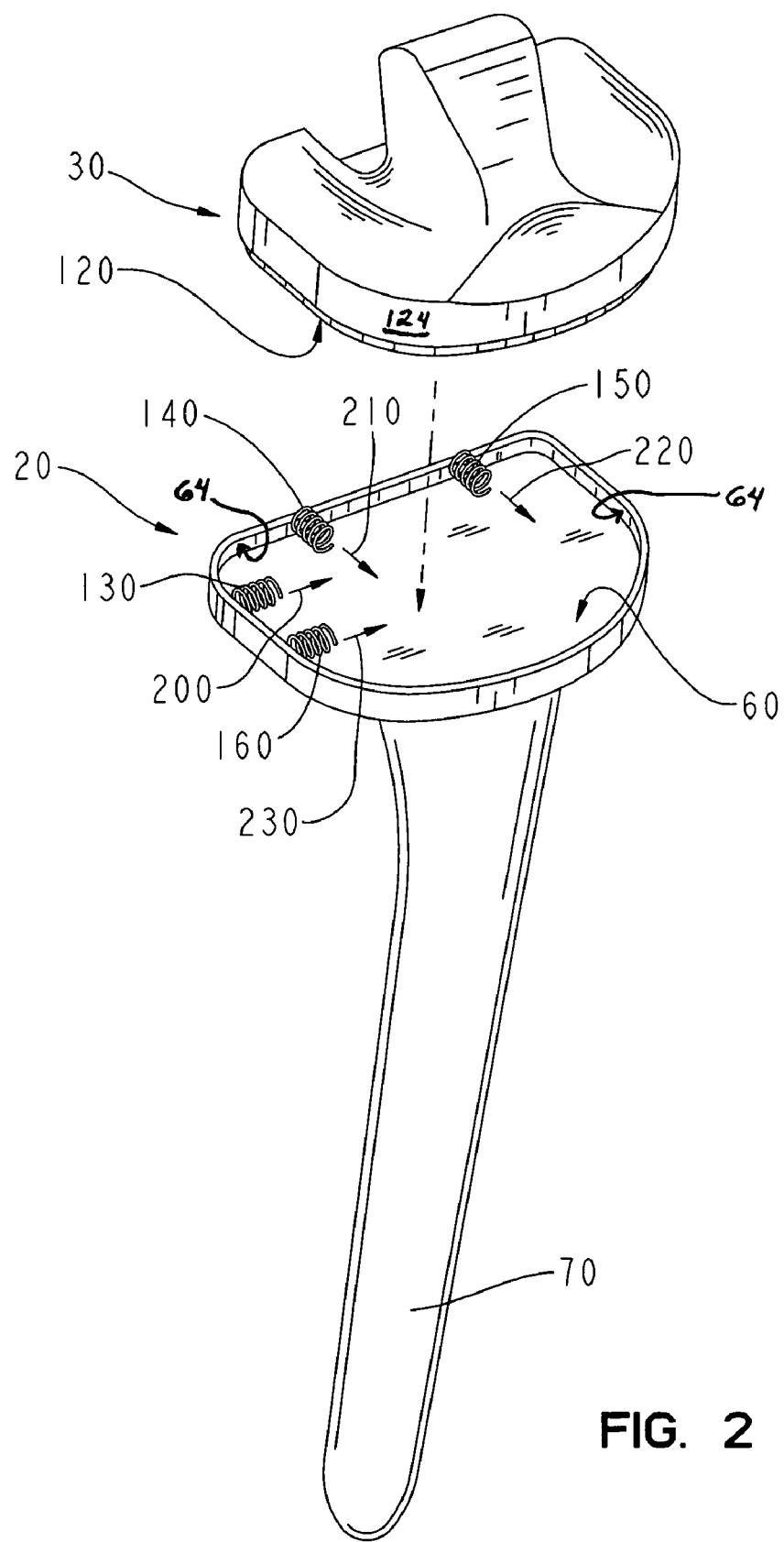
FIG. 2 shows an exploded perspective view of the tibial component, the bearing, and the micro-motion dampers of the exemplary knee assembly of FIG. 1.

FIG. 2 shows an exploded perspective view of tibial component 20, bearing 30, micro-motion damper 130, micro-motion damper 140, micro-motion damper 150, and micro-motion damper 160. In the exemplary embodiment shown in FIG. 2, micro-motion damper 130, micro-motion damper 140, micro-motion damper 150, and micro-motion damper 160 are each formed by a coiled metallic spring and peripherally spaced apart on inner sidewall 64 of tibial baseplate 60. In alternative embodiments, micro-motion damper 130, micro-motion damper 140, micro-motion damper 150, and micro-motion damper 160 each may be a comparable bowed or flexed metal strip or metal tape, a comparable rubber cylinder, a comparable compressible gas filled cylinder, or any other resilient material or assembly of any size, shape, spring rate, and/or positioning on tibial baseplate 60 suitable for desirable damping of micro-motion between bearing 30 and tibial baseplate 60. In the exemplary embodiment, exemplary micro-motion damper 130, exemplary micro-motion damper 140, exemplary micro-motion damper 150, and exemplary micro-motion damper 160 are each welded, cemented, or otherwise suitably fixedly coupled to inner sidewall 64. However, it is noted that in alternative embodiments exemplary micro-motion damper 130, exemplary micro-motion damper 140, exemplary micro-motion damper 150, and exemplary micro-motion damper 160 may be suitably fixedly coupled to sidewall 124 of bearing 30 in addition to or in lieu of inner sidewall 64, while in other alternative embodiments exemplary micro-motion damper 130, exemplary micro-motion damper 140, exemplary micro-motion damper 150, and exemplary micro-motion damper 160 may not be fixedly coupled to either bearing 30 or tibial baseplate 60. In any event, it is also noted that in alternative embodiments exemplary micro-motion damper 130, exemplary micro-motion damper 140, exemplary micro-motion damper 150, and exemplary micro-motion damper 160 may be replaced with a single one or any other suitable number of suitably sized, shaped, spring rated, and/or positioned micro-motion dampers, which may be distinct from bearing 30 and tibial baseplate 60 in some embodiments or integral to at least one of bearing 30 or tibial baseplate 60 in other embodiments.

Micro-motion damper 130, micro-motion damper 140, micro-motion damper 150, and micro-motion damper 160 are sandwiched and compressed between inner sidewall 64 of baseplate 60 and sidewall 124 of bearing 30. It should be appreciated that bearing 30 is held in tibial baseplate 60 by a clearance fit, a locking key arrangement, grooves, dovetails, rails, suitable expandable structure(s), or any other suitable structure(s).

In operation, micro-motion damper 130 exerts an expansion force on bearing 30 along directional line 200, micro-motion damper 140 exerts an expansion force on bearing 30 along directional line 210, micro-motion damper 150 exerts an expansion force on bearing 30 along directional line 220, and micro-motion damper 160 exerts an expansion force on bearing 30 along directional line 230. The expansion forces reduce any slack or play (and hence, damp micro-motion) between bearing 30 and tibial baseplate 60 and damp micro-motion of bearing 30 relative to tibial baseplate 60.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A modular implant, comprising:
   a first orthopaedic component;
   a second orthopaedic component releasably coupled to the first orthopaedic component;
   a first micro-motion damper interposed between the first orthopaedic component and the second orthopaedic component, the first micro-motion damper damping micro-motion between the first and second orthopaedic components in a first direction; and
   a second micro-motion damper interposed between the first orthopaedic component and the second orthopaedic component, the second micro-motion damper damping micro-motion between the first and second orthopaedic components in a second direction, the first and second directions being coplanar and the first direction being transverse to the second direction, at least one of the micro-motion dampers including a coiled spring.

2. A modular implant, comprising:
   a first orthopaedic component;
   a second orthopaedic component releasably coupled to the first orthopaedic component;
   a first micro-motion damper interposed between the first orthopaedic component and the second orthopaedic component, the first micro-motion damper damping micro-motion between the first and second orthopaedic components in a first direction; and
   a second micro-motion damper interposed between the first orthopaedic component and the second orthopaedic component, the second micro-motion damper damping micro-motion between the first and second orthopaedic components in a second direction, the first and second directions being coplanar and the first direction being transverse to the second direction, at least one of the micro-motion dampers including a metallic tape.

3. A knee prosthesis for insertion between a femur and a tibia, comprising:
   a tibial baseplate;
   a modular bearing removably mounted to the tibial baseplate;
   a first resilient component positioned between the tibial component and the bearing, the first resilient component biasing the bearing relative to the baseplate in a first direction; and
   a second resilient component positioned between the tibial component and the bearing, the second resilient component biasing the bearing relative to the baseplate in a second direction, the first and second directions being coplanar and the first direction being transverse to the second direction, at least one of the resilient components including a coiled spring.

4. A knee prosthesis for insertion between a femur and a tibia, comprising:
   a tibial baseplate;
   a modular bearing removably mounted to the tibial baseplate;
   a first resilient component positioned between the tibial component and the bearing, the first resilient component biasing the bearing relative to the baseplate in a first direction; and
   a second resilient component positioned between the tibial component and the bearing, the second resilient component biasing the bearing relative to the baseplate in a second direction, the first and second directions being coplanar and the first direction being transverse to the second direction, at least one of the resilient components including a flexed strip.

5. A modular joint prosthesis for insertion between two bones at a skeletal joint, the modular joint prosthesis comprising:
   a first orthopaedic component having a modular mounting portion;
   a second orthopaedic component having a modular mounting portion, the first orthopaedic component modular mounting portion engaging the second orthopaedic component modular mounting portion in releasable coupled relationship, the first orthopaedic component and second orthopaedic component defining play between them permitting the first orthopaedic component to move relative to the second orthopaedic component;
   means for releasably locking the first orthopaedic component adjacent to the second orthopaedic component; and
   means for resiliently biasing the first orthopaedic component relative to the second orthopaedic component to reduce movement between them, the means for biasing being separate from the means for releasably locking, the first orthopaedic component comprising a tibial bearing having a joint articulation surface and a modular mounting portion and the second orthopaedic component comprising a tibial baseplate having a portion implantable on the bone and a modular mounting portion, the tibial baseplate modular mounting portion comprising a recess with an inner sidewall; the tibial bearing modular mounting portion comprising a bottom portion receivable in the baseplate recess, the bottom portion including a peripheral sidewall corresponding to the inner sidewall of the baseplate recess; and the means for biasing comprising a resilient member mounted to the baseplate within the recess, the bearing peripheral sidewall being engageable with the resilient member upon insertion of the bearing into the baseplate recess and the bearing peripheral sidewall being disengageable from the resilient member upon removal of the bearing from the baseplate recess.

6. A modular joint prosthesis for insertion between two bones at a skeletal joint, the modular joint prosthesis comprising:

a first orthopaedic component having a modular mounting portion;

a second orthopaedic component having a modular mounting portion, the first orthopaedic component modular mounting portion engaging the second orthopaedic component modular mounting portion in releasable coupled relationship, the first orthopaedic component and second orthopaedic component defining play between them permitting the first orthopaedic component to move relative to the second orthopaedic component;

means for releasably locking the first orthopaedic component adjacent to the second orthopaedic component; and means for resiliently biasing the first orthopaedic component relative to the second orthopaedic component to reduce movement between them, the means for biasing being separate from the means for releasably locking, the first orthopaedic component comprising a tibial bearing having a joint articulation surface and a modular mounting portion and the second orthopaedic component comprising a tibial baseplate having a portion implantable on the bone and a modular mounting portion, the tibial baseplate modular mounting portion comprising a recess with an inner sidewall; the tibial bearing modular mounting portion comprising a bottom portion receivable in the baseplate recess, the bottom portion including a peripheral sidewall corresponding to the inner sidewall of the baseplate recess; and the inner sidewall of the tibial baseplate modular mounting portion and the peripheral sidewall of the tibial bearing modular mounting portion defining a gap between them, the means for resiliently biasing comprising a resilient member positioned within the gap.

7. A modular joint prosthesis for insertion between two bones at a skeletal joint, the modular joint prosthesis comprising:

a first orthopaedic component having a modular mounting portion;

a second orthopaedic component having a modular mounting portion, the first orthopaedic component modular mounting portion engaging the second orthopaedic component modular mounting portion in releasable coupled relationship, the first orthopaedic component and second orthopaedic component defining play between them permitting the first orthopaedic component to move relative to the second orthopaedic component;

means for releasably locking the first orthopaedic component adjacent to the second orthopaedic component; and means for resiliently biasing the first orthopaedic component relative to the second orthopaedic component to reduce movement between them, the means for biasing being separate from the means for releasably locking, the means for releasably locking comprising at least one means selected from the group consisting of a locking key, a groove, a dovetail, and a rail.

8. A modular joint prosthesis for insertion between two bones at a skeletal joint, the modular joint prosthesis comprising:

a first orthopaedic component having a modular mounting portion;

a second orthopaedic component having a modular mounting portion, the first orthopaedic component modular mounting portion engaging the second orthopaedic component modular mounting portion in releasable coupled relationship, the first orthopaedic component and second orthopaedic component defining play between them permitting the first orthopaedic component to move relative to the second orthopaedic component;

means for releasably locking the first orthopaedic component adjacent to the second orthopaedic component; and means for resiliently biasing the first orthopaedic component relative to the second orthopaedic component to reduce movement between them, the means for biasing being separate from the means for releasably locking, the means for biasing comprising at least one means selected from the group consisting of a coiled spring, a flexed strip, a resilient cylinder, and a compressible gas filled cylinder.

9. A modular joint prosthesis for insertion between two bones at a skeletal joint, the modular joint prosthesis comprising:

a first orthopaedic component having a modular mounting portion;

a second orthopaedic component having a modular mounting portion, the first orthopaedic component modular mounting portion engaging the second orthopaedic component modular mounting portion in releasable coupled relationship, the first orthopaedic component and second orthopaedic component defining play between them permitting the first orthopaedic component to move relative to the second orthopaedic component;

means for releasably locking the first orthopaedic component adjacent to the second orthopaedic component; and means for resiliently biasing the first orthopaedic component relative to the second orthopaedic component to reduce movement between them, the means for biasing being separate from the means for releasably locking, the means for biasing comprises:

first means for biasing the first orthopaedic component relative to the second orthopaedic component in a first direction; and second means for biasing the first orthopaedic component relative to the second orthopaedic component in a second direction, the first and second directions being coplanar and the first direction being transverse to the second direction.

* * * * *